(12) United States Patent
Naik et al.

(10) Patent No.: US 8,106,189 B2
(45) Date of Patent: Jan. 31, 2012

(54) PROCESS FOR PREPARATION OF TRIAZOL-BENZODIAZEPINE DERIVATIVES

(75) Inventors: Anil M. Naik, Mumbai (IN); Shrikant D. Sawant, Mumbai (IN); Girish A. Kavishwar, Mumbai (IN); Smita G. Kavishwar, Mumbai (IN)

(73) Assignee: Centaur Chemicals Pvt Ltd, Mumbai (IN)

( * ) Notice: Subject to any disclaimer, the term of this patent is extended or adjusted under 35 U.S.C. 154(b) by 705 days.

(21) Appl. No.: 12/193,857

(22) Filed: Aug. 19, 2008

(65) Prior Publication Data

US 2009/0093629 A1   Apr. 9, 2009

(30) Foreign Application Priority Data

Oct. 3, 2007   (IN) .................. 1951/MUM/2007

(51) Int. Cl.
*C07D 487/12* (2006.01)
*C07D 491/00* (2006.01)
(52) U.S. Cl. ........................ 540/560; 540/566
(58) Field of Classification Search .............. 540/560, 540/566
See application file for complete search history.

(56) References Cited

U.S. PATENT DOCUMENTS 3,987,052 A   10/1976   Hester

FOREIGN PATENT DOCUMENTS

DE    3413709 A    10/1984
HR    P20010081 A1    12/2005

OTHER PUBLICATIONS

Banks et al. "Development of Methodology for the Rapid Incorporation of Carbon-13 Into 1,2,4-Triazolo Systems From Carbon Dioxide" Tetrahedron Letters, vol. 30, No. 47, pp. 6473-6476, 1989.
Bechtel et al., Blood Level, Distribution, Excretion and Metabolite Pattern of [14C]-Brotizolam in the Rat, Dog, and Rhesus Monkey, Arzneimitterlforschung Mar. 1986: 36(3A) pp. 568-573.

*Primary Examiner* — Brenda Coleman
(74) *Attorney, Agent, or Firm* — Cardinal Law Group

(57) ABSTRACT

An improved process for preparation of triazol-benzodiazepine derivatives, such as alprazolam, triazolam, brotizolam and etizolam, is presented. The process comprises a cyclization reaction of compound Formula B in toluene with catalytic amount of p-toluene sulphonic acid to obtain the triazol-benzodiazepine derivative of Formula C:

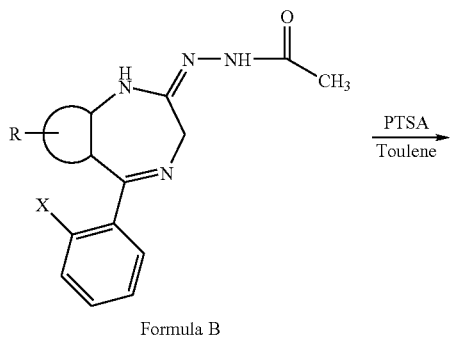

Formula B

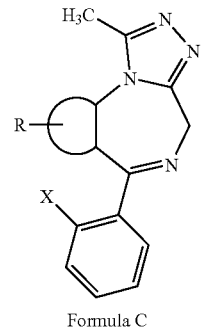

Formula C wherein R is,

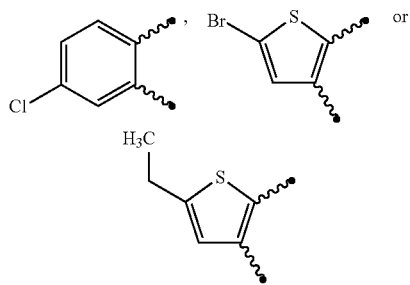

and X is hydrogen or halogen.

8 Claims, No Drawings

PROCESS FOR PREPARATION OF TRIAZOL-BENZODIAZEPINE DERIVATIVES

This application claims the priority of Indian Patent Application No. 1951/MUM/2007, filed Oct. 3, 2007.

FIELD OF INVENTION

This invention relates to an improved process for preparation of pharmaceutically active triazol-benzodiazepine derivatives such as alprazolam, triazolam, brotizolam and etizolam etc. These pharmaceutically active agents are short acting drugs in the benzodiazepine class used to treat anxiety disorder and as an adjunctive treatment for depression.

BACKGROUND OF INVENTION

Triazole-benzodiazepine derivatives, such as alprazolam, triazolam, brotizolam, etizolam, etc., are marketed for therapeutic indications such as anxiety disorder and adjunctive treatment for depression.

The general scheme for preparation of the triazole-benzodiazepine derivatives is as follows:

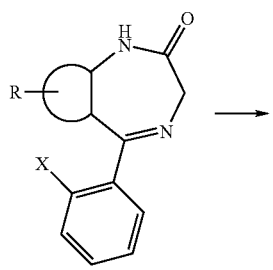

Formula A

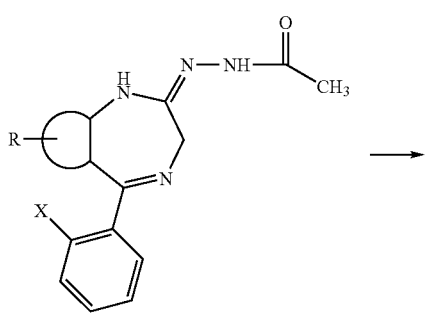

Formula B

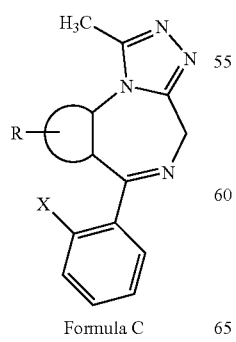

Formula C where R is

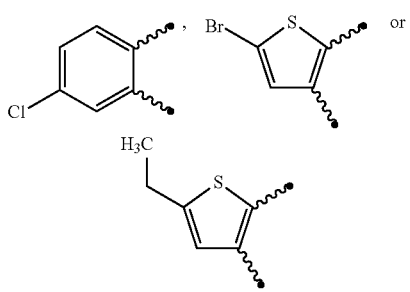

(the spiral line indicates the side that is attached to the benzodiazepine nucleus), and X is hydrogen or halogen, i.e. chlorine, fluorine, bromine or iodine.

From the above mentioned general scheme, it appears that there is a common strategy for synthetic preparation of the triazole-benzodiazepine derivatives involves triazol ring formation as a common step. The benzodiazepine moiety (Formula A) required for synthesis can be prepared from corresponding suitable benzophenone derivatives which is commonly described in the literature. The synthesis of triazol-benzodiazepine involves a common step of cyclization and formation of the triazol ring from acetyl hydrazone derivatives (Formula B) derived from different benzodiazepine. The formation of acetyl hydrazone derivatives and its cyclization forms a common synthetic scheme in various triazol-benzodiazepines, such as alprazolam, triazolam, brotizolam and etizolam etc.

Therefore, the present invention aims to develop a convenient process of cyclization of acetyl hydrazone derivatives (Formula B) to obtain Formula C.

U.S. Pat. No. 3,987,052 to Hester et al. describes various strategies for the formation of benzodiazepine-triazol moieties in patent which involves the following steps:

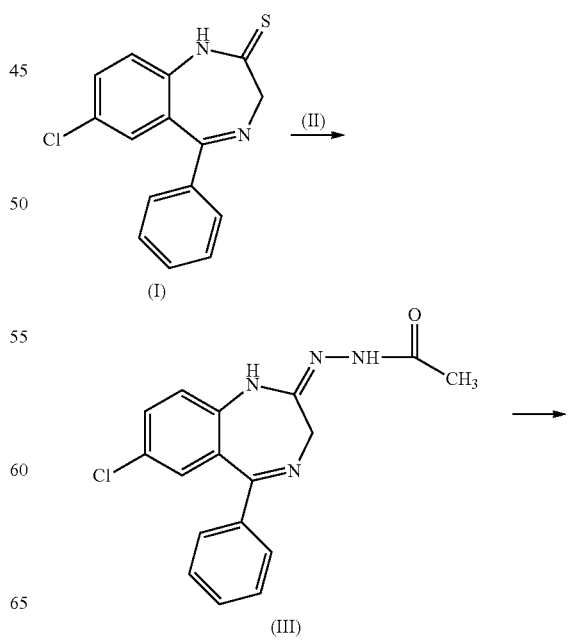

-continued

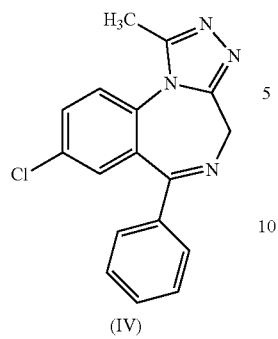

(IV)

According to the above patent, 1,3 dihydro-5-phenyl-2H-1,4 benzodiazepine-2-thione of formula (I) in ethanol when condensed with acetyl hydrazide (II) at a temperature range of 60-120° C. for 24 hours obtained a crude mixture comprising of corresponding 2-(2-acetyl hydrazino)-5-phenyl-3H-1,4 benzodiazepine (III) and the corresponding 8-chloro-1-methyl-6-phenyl-4H-s-triazolo[4,3-I] [1,4]benzodiazepine (IV). Further purification by conventional methods, such as extraction or chromatography, is required to obtain the compound IV with a yield of 47.7%.

From commercial point of view, above said preparation is tedious and lengthy as well as expensive due to low yield due to concomitant formation of compounds III and IV.

According to Croatian Patent No. HR-P2001000081, alprazolam was prepared by cyclization of acetyl hydrazone using tri-ethyl ortho acetate in presence of catalyst as follows:

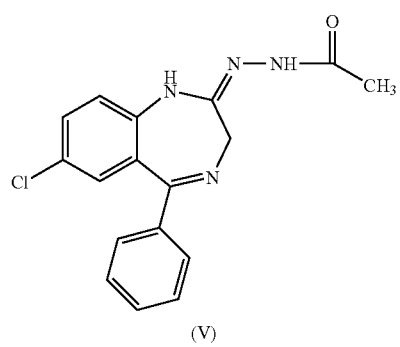

(V)

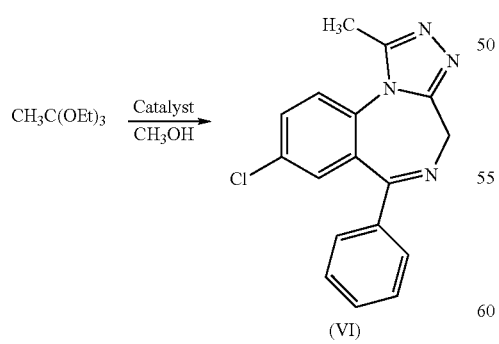

(VI)

Tri-ethyl ortho acetate is a flammable liquid which is difficult to handle on industrial scale. Additionally, the catalyst used in the above cyclization process is expensive, as well as being unavailable commercially, due to its high manufacturing cost.

In patent DE 3413709 A, the title compound I

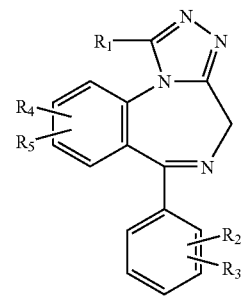

I (R1=H, C1-3 alkyl; R2 to R5=H, C1-3 alkyl, halo) were prepared by mesylating the alcohol II

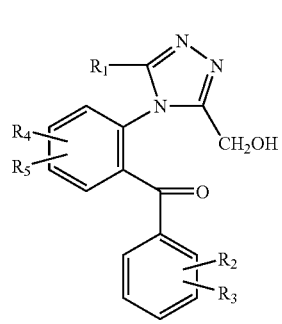

II (R=H) and cyclizing the product III

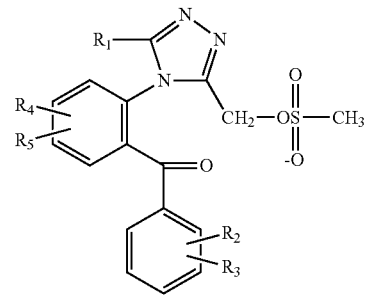

III (R=SO$_2$Me) with aqueous NH$_4$OH—C1-3 alkanol. Mesylating the alcohol II (R, R2—R4=H, R1=Me, R5=Cl) in DMF, THF, and NEt$_3$ with MeSO$_2$Cl-THF at −10° C. over 30 min, then stirring 30 min, filtering, and treating the filtrate (containing the compound III (R=SO$_2$Me)) with aqueous NH$_4$OH—MeOH gave alprazolam (I, R1=Me, R2—R4=H, R5=Cl).

The drawbacks of the above mentioned processes are requiring more operations to obtain the triazol-benzodiazepine derivatives with critical parameters, and requiring the use of reagents such as methane sulphonyl chloride-tetra hydro furan (THF) at −10° C.

Therefore, there is a need in the art to provide a cost-effective and ecologically friendly process for preparation of triazol-benzodiazepine derivatives, such as alprazolam, triazolam, brotizolam and etizolam. Accordingly the present invention provides a process which is devoid of the use of expensive and hazardous reagents, and of critical reaction parameters. Also, the solvent used as reaction medium is recovered to a greater extent after the completion of reaction which makes the process commercially applicable for industrial scale.

SUMMARY OF INVENTION

Therefore, the present invention utilizes commercially available solvent like toluene and commercially available catalyst like p-toluene sulphonic acid to exert good yield with purity thereby making the process cost effective.

An object of the present invention is to provide a commercially suitable process for the preparation of triazol-benzodiazepine derivatives, which involves a low number of operations and uses non-hazardous reagents and solvents.

Another objective of the invention is to provide cost effectiveness and environment friendly process over the existing prior arts.

This invention mainly directed to industrially applicable and commercially feasible process for the preparation of triazol-benzodiazepine derivatives, such as alprazolam, triazolam, brotizolam, etizolam, etc. The improved process is carried out under milder reaction conditions and is devoid of highly toxic reagents.

The preparations of triazol-benzodiazepine derivatives involving the following common synthetic step:

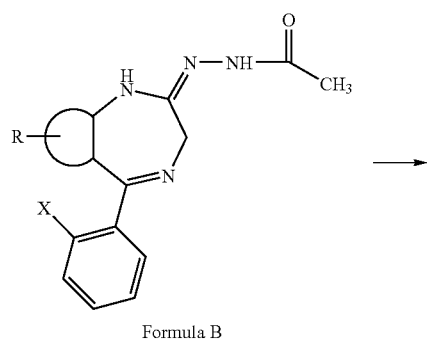

Formula B

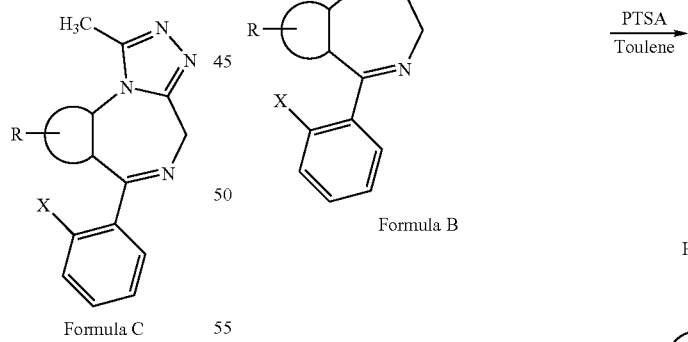

Formula C where R and X are defined above. Preferably, the reaction takes place in toluene at reflux temperature in the presence of p-toluene sulphonic acid (PTSA).

In an embodiment, the intermediate for alprazolam, 2-(2-acetyl hydrazino)-7-chloro-5-phenyl-2H-1,4 benzodiazepine (acetyl hydrazone), is cyclicized in toluene at the reflux temperature in the presence of p-toluene sulphonic acid (PTSA), preferably for 10-12 hours, to obtain 8-chloro-1-methyl-6-phenyl-4H-s-trizolo[4 3-I] [1,4]benzodiazepine(alprazolam) in good yield without formation of side products.

In an another embodiment, the intermediate for triazolam, 2-(2-acetyl hydrazine)-7-chloro-5-(2-chloro phenyl)-3H-1,4-bezodiazepine(chloroacetylhydrazone), is cyclicized in toluene at the reflux temperature in the presence of p-toluene sulphonic acid (PTSA), preferably for 10-12 hours, to obtain triazolam in good yield without formation of side products.

In an another embodiment the intermediate, for brotizolam, 2-bromo-4-(2-chlorophenyl)-7-acetyl hydrazido-6H-thieno[3 2 f]-1,4-dizapine, is cyclized in toluene at the reflux temperature in the presence of p-toluene sulphonic acid (PTSA), preferably for 10-12 hours, to obtain brotizolan in good yield without formation of side products.

In an another embodiment the intermediate for etizolam, 7-(acetyl hydrazido)-4-(2-chloropheny)-2-ethyl-6H-thieno[3 2 f]-1,4-dizapine, is cyclized in toluene at the reflux temperature in the presence of p-toluene sulphonic acid (PTSA), preferably for 10-12 hours, to obtain etizolam in good yield without formation of side products.

DETAIL DESCRIPTION OF INVENTION

While the invention will now be described in detail in connection with certain preferred and optional embodiments, so that various aspects thereof may be more fully understood and appreciated, it is not intended to limit the invention to these particular embodiments.

The method described herein further provides substantial benefits relative to previously used or suggested production methods. For example, the starting materials, intermediates, liquid media, and catalysts used are relatively easier to handle and to dispose off, if necessary. Importantly, the present method provides high yields of about 75 to 80% improvement over the methods of existing prior art.

This improved process for preparation of triazole-benzodiazapine derivatives carried out in single step which has been depicted as follows:

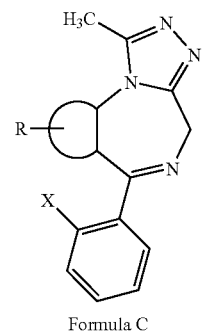

Formula C where R and X are defined above. The reaction preferably takes place in toluene at reflux temperature (100-110° C.) in the presence of p-toluene sulphonic acid (PTSA). The molar ratio of the compound of Formula B to toluene (solvent) is about 1:25 to about 1:45, preferably about 1:35 to about 1:40. The molar ratio of Formula-B to PTSA (catalyst) is at least 300:1, preferably about 300:1.1 to about 300:1.5. The cyclization of Formula B is carried out at a temperature of about 100-110° C., i.e. the reflux temperature of the solvent (toluene), for about 10-12 hours.

The reaction mass (after completion of reaction) is cooled abruptly for 30 min. to 25 to 30° C. and then gradually cooled to 10 to 15° C. and stirrer for 4-5 hrs. to obtain a solid or wet cake of compound Formula C. (alprazolam, triazolam, brotizolam, or etizolam).

The wet cake obtained from said cyclization reaction is slurried with an aliphatic solvent, (such as methanol or ethanol), an ester (such as ethyl acetate), or an aromatic solvent (such as toluene) for up to 2 hrs to obtain a pure Formula C.

The process described above can be used to make triazole-benzodiazapine derivatives (alprazolam, triazolam, brotizolam, etizolam, etc.) having a purity of about 99.5 to 99.9% and with about 75 to 80% yield.

In an embodiment of the present invention, the intermediate for alprazolam, 2-(2-acetyl hydrazino)-7-chloro-5-phenyl-2H-1,4 benzodiazepine(acetyl hydrazone) (Formula B) is cyclicized in toluene at reflux temperature in presence of p-toluene sulphonic acid for 10-12 hours, to obtain 8-chloro-1-methyl-6-phenyl-4H-s-trizolo[4 3-I][1,4] benzodiazepine referred as Alprazolam with yield of about 75-80% with minimal or negligible formation of side products.

Thus, according to preferred embodiment, acetyl hydrazone of formula B is mixed with excess moles of toluene, followed by distillation of 0.2% of toluene at 110 to 112° C. The reaction mixture is cooled to 90 to 95° C., followed by the addition of p-toluene sulphonic acid in catalytic amount (about 1 to about 1.5% w/w). The reaction mixture is refluxed for 1 to 20 hrs; preferably 10 to 12 hrs. The progress of the reaction is monitored by thin layered chromatography (TLC). After completion, the reaction mixture is cooled to 25 to 30° C., then further cooled 0 to 15° C. and stirred at the same temperature for 4 to 5 hrs. The solids precipitated were filtered and washed with cold toluene and finally purified by isopropanol.

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in this example.

EXAMPLE 1

General Preparation of triazole-benzodiazepine Derivatives

The following general scheme and reaction conditions illustrate the formation of the triazole-benzodiazepine derivatives:

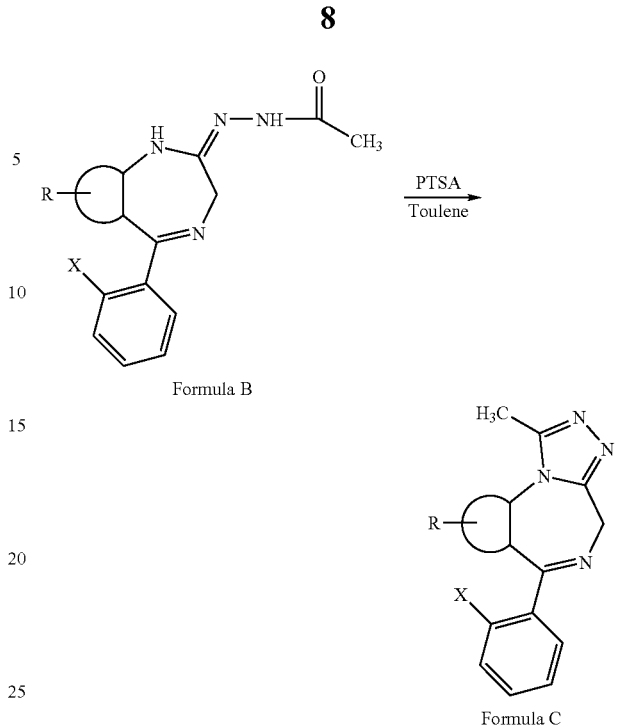

Formula B

Formula C where R and X are defined above.

Formula B (0.36 mole) and toluene (11.75 moles) were added to a round bottom (RB) flask. 0.94 mole of toluene are distilled out with a Dean-Stark apparatus for water removal at 110-112° C. The mixture was then cooled to 90-95° C. and p-toluene sulphonic acid (0.0012 mole) was added. The reaction mixture was refluxed at 105-110° C. for 10-12 hrs. At the end of the reaction (as indicated by TLC), the reaction mixture was cooled to 25-30° C. The reaction mass was then further cooled to 10-15° C. and stirred at same temperature for 4-5 hrs. The solids precipitated containing crude Formula C were filtered and washed with cold toluene. The Formula C thus obtained was further purified from isopropanol with a yield of 75-80%.

EXAMPLE 2

Preparation of Alprazolam 2-(2-acetyl hydrazino)-7-chloro-5-phenyl-2H-1,4 benzodiazepine (117.5 g; 0.36 mole) and toluene (11.75 mole.) were added to a RB flask. 0.94 mole of toluene was distilled out at 110-112° C. The reaction mixture was cooled to 90-95° C. and charged with p-toluene sulphonic acid (0.0012 mole). The reaction mixture was then refluxed at 105-110° C. for 10-12 hrs with a Dean-Stark apparatus for water removal. At the end of the reaction (as indicated by TLC), reaction mixture was cooled to 25-30° C. The reaction mass was then further cooled to 10-15° C. and stirred at same temperature for 4-5 hrs. The solids precipitated were filtered and washed with cold toluene to obtain crude 8-chloro-1-methyl-6-phenyl-4H-s-trizolo[4 3-I][1,4] benzodiazepine (alprazolam). The crude alprazolam was purified from isopropanol to obtain 80% yield of pure alprazolam.

EXAMPLE 3

Preparation of Triazolam

The following steps are used in making triazolam: 1) charged 2-(2-acetyl hydrazine)-7-chloro-5-(2-chloro phenyl)-3H-1,4-bezodiazepine(chloro acetyl hydrazone) (130 g; 0.36 mole) and toluene (11.75 moles.) in a 2.0 L RB flask; 2) distilled out 0.94 moles of toluene at 110-112° C.; 3) cooled the reaction mixture to 90-95° C. and charged p-toluene sulphonic acid (0.0012 mole); 4) refluxed the reaction mixture at 105-110° C. for 10-12 hrs with Dean-Stark apparatus for water removal; 4) at the end of the reaction (as indicated by TLC), cooled the reaction mixture to 25-30° C.; 5) further cooled the reaction mixture to 10-15° C. and stirred at same temperature for 4-5 hrs; 5) filtered and washed precipitated solid with cold toluene (130 ml) to obtain crude triazolam (108-113.5 g); 5) obtained purified triazolam at 77% yield by purifying the crude triazolam from isopropanol.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A process for preparation of triazol-benzodiazepine of Formula-C

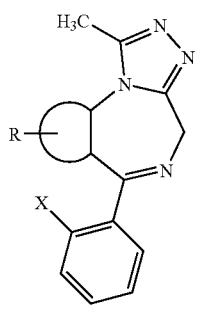

Formula C wherein R is,

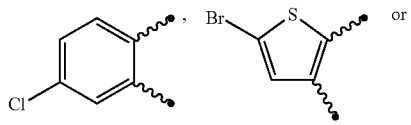

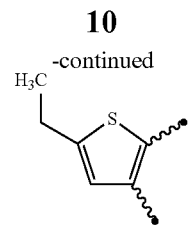

and X is hydrogen or halogen, the process comprising the step of cyclicizing the compound of Formula B

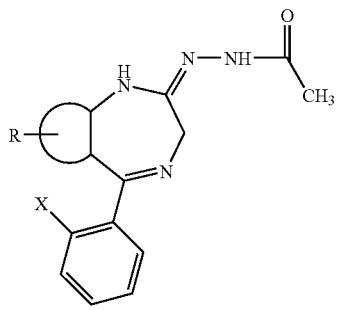

Formula B in the presence of p-toluene sulphonic acid as catalyst in toluene as the reaction medium to obtain compound of Formula-C.

2. The process of claim 1, wherein the cyclization of Formula B is carried out at a temperature of 110 to 110° C. for 10 to 12 hrs.

3. The process of claim 1, further comprising the steps of cooling the reaction mass, after completion of the cyclicizing step, to 25-30° C. and further cooling to 10-15° C. to obtain a solid containing the compound of Formula-C.

4. The process of claim 3, further comprising a step of stirring the reaction mass at 10-15° C. for 4 to 5 hrs to obtain a solid or a wet cake containing the compound of Formula-C.

5. The process of claim 1, wherein the molar ratio of said Formula-B to p-toluene sulphonic acid is at least 1:300.

6. The process of claim 1, further comprising a step of treating a dry solid cake obtained from the cyclization with a solvent selected from the group consisting of aliphatic solvent, ester, and aromatic solvent to obtain a pure Formula-C.

7. The process of claim 1, wherein said process is used in the manufacture of alprazolam, triazolam, brotizolam or etizolam with about 99.9% purity and about 75-80% yield.

8. The process of claim 1, wherein said compound of Formula-C is selected from the group consisting of alprazolam, triazolam, brotizolam and etizolam.

* * * * *